United States Patent
Bonnard et al.

(10) Patent No.: US 7,780,737 B2
(45) Date of Patent: Aug. 24, 2010

(54) BALL-TYPE TRIPLE-JOINT IMPLANT SYSTEM FOR UPPER OR LOWER LIMBS

(75) Inventors: Olivier Bonnard, 21 rue Duquesne, 69330 Meyzieu (FR); Philippe Bauchu, 4 rue Clotilde Bizolon, 69002 Lyons (FR); Alain Cypres, 445 Chemin de la Grange du Bois, 42190 St. Nizier Sous Charlieu (FR); Arnaud Fiquet, 4 montée des Lilas, 69300 Caluire (FR); Philippe Girardin, Puy Money, 42600 Lezigneux (FR); Daniel Noyer, Hameau le Fourgeon, 38200 Luzinay (FR); Jean-Pierre Moulin, Lyons (FR); Christophe Roy, Lyons (FR)

(73) Assignees: Ortho ID, Bron (FR); Olivier Bonnard, Meyzieu (FR); Philippe Bauchu, Lyon (FR); Alain Cypres, Sous Charlieu (FR); Arnaud Fiquet, Caluire (FR); Philippe Girardin, Lezigneux (FR); Daniel Noyer, Luzinay (FR)

( * ) Notice: Subject to any disclaimer, the term of this patent is extended or adjusted under 35 U.S.C. 154(b) by 230 days.

(21) Appl. No.: 11/659,721

(22) PCT Filed: Aug. 9, 2004

(86) PCT No.: PCT/FR2004/002110

§ 371 (c)(1),
(2), (4) Date: Apr. 12, 2007

(87) PCT Pub. No.: WO2006/027422

PCT Pub. Date: Mar. 16, 2006

(65) Prior Publication Data
US 2007/0255418 A1 Nov. 1, 2007

(51) Int. Cl.
A61F 2/42 (2006.01)
A61F 2/32 (2006.01)
(52) U.S. Cl. ............... 623/21.11; 623/21.15; 623/22.18
(58) Field of Classification Search .... 623/18.11–23.47
See application file for complete search history.

(56) References Cited

U.S. PATENT DOCUMENTS 3,916,451 A 11/1975 Buechel et al.

(Continued)

FOREIGN PATENT DOCUMENTS

DE 44 28 407 A1 2/1996

(Continued)

Primary Examiner—Bruce E Snow
(74) Attorney, Agent, or Firm—Oliff & Berridge, PLC

(57) ABSTRACT

The invention relates to a system which is used to replace ball bone joints. The inventive system consists of: a bone anchoring shell (1) comprising a smooth articular surface (7) on the inner concave face thereof; a prosthesis (5) comprising a polished ball (4) and a neck (6) which is characterised in that it is smooth and slightly flared, in order to enable a wear-free low friction movement; and a mobile articular cup (3) which slides (i) on the ball (4) and the neck (6) of a prosthesis (5) and (ii) in the smooth cavity (7) of the bone anchoring shell (1) and which is characterised in that the opening (8) in said cup (3) tapers towards the center thereof, with an inside diameter (9) of equal to or less than that of the ball (4), such that the flared part adapts perfectly to the flared neck (6) in all of the respective positions of the mobile parts.

10 Claims, 3 Drawing Sheets

U.S. PATENT DOCUMENTS

| | | |
|---|---|---|
| 4,642,123 A | 2/1987 | Noiles |
| 4,678,472 A | 7/1987 | Noiles |
| 4,801,301 A | 1/1989 | Noiles |
| 4,919,669 A | 4/1990 | Lannelongue |
| 4,950,299 A | 8/1990 | Noiles |
| 4,955,916 A | 9/1990 | Carignan et al. |
| 4,960,427 A | 10/1990 | Noiles |
| 4,978,356 A | 12/1990 | Noiles |
| 5,916,270 A * | 6/1999 | Lipman .................. 623/22.15 |
| 6,042,611 A | 3/2000 | Noiles |
| RE38,409 E | 1/2004 | Noiles |
| 6,986,792 B2 * | 1/2006 | McLean et al. .......... 623/22.29 |
| 2003/0171817 A1 | 9/2003 | Rambert et al. |
| 2004/0225370 A1 | 11/2004 | Cruchet et al. |

FOREIGN PATENT DOCUMENTS

| | | |
|---|---|---|
| FR | 2 558 721 | 8/1985 |
| FR | 2 610 515 | 8/1988 |
| FR | 2 618 065 | 1/1989 |
| FR | 2 652 498 | 4/1991 |
| FR | 2 662 930 A1 | 12/1991 |
| FR | 2 692 776 A1 | 12/1993 |
| FR | 2 703 904 | 10/1994 |
| FR | 2 807 315 A1 | 10/2001 |
| FR | 2 850 861 A1 | 8/2004 |

* cited by examiner

BALL-TYPE TRIPLE-JOINT IMPLANT SYSTEM FOR UPPER OR LOWER LIMBS

I. TECHNICAL FIELD AND PRIOR ART

The devices known at present for forming an articular bearing in order to replace the ball-type joints of the upper or lower limb are of four types:

1. Cups cemented in the bone cavity and designed to receive a prosthesis ball, cf. patent applications Lannelongue 87 01524 and Gramont 87 10495.
2. Simple mobile cups referred to as "intermediate" which articulate on a prosthesis ball and in the bone cavity on the remainder of the cartilage, since they are not fixed in said bone cavity, cf. patent application Flot 84 01330.
3. Metal cups referred to as "cementless", which are introduced with force into the bone cavity that has been prepared using a shaping instrument, and which are equipped with a fixed articular insert designed to receive a prosthesis ball, cf. patent applications Dupuy 93 04657 and Colombier 89 13366.
4. Metal cups referred to as cementless and externally similar to type 3, but having a polished concave inner face for receiving a mobile cup which is articulated both within this concavity and also on a prosthesis ball, cf. patent FR 2 662 930 A1 (Bouvet). This latter type of implant, although attractive in terms of its principle, is somewhat disappointing in the medium term since, because the ball is retained in the mobile cup, the latter is subjected to wear, with considerable formation of debris that may lead to surgical revision, or even to luxation that requires replacement of the implants.

II. PRINCIPLES AND EXPECTED ADVANTAGES OF THE INVENTION

It is important and economic to offer patients implants which are designed to replace the joints of the upper or lower limbs and which are stables and free from luxation, even in cases of great mobility, particularly in circumduction, and whose wear is minimal, in order to reduce the number of prosthesis replacements in an elderly population whose life expectancy is increasing but for whom revision procedures are onerous in terms of mortality and morbidity. The triple joint forming the subject matter of the invention is produced, for the first joint, between the outer face of a mobile cup made of plastic biocompatible material, and between the inside of a bone-anchoring shell made of rigid biocompatible material and having a face with a substantially hemispherical concavity polished and free of bumps, cavities or reliefs that could wear said mobile cup or impede its free clearance when the latter is stressed in rotary displacement by the neck of the prosthesis; and, for the second joint, between the polished articular surface of the ball of a prosthesis and between the inner face of the mobile cup whose surface area is preferably greater than a hemisphere of diameter similar to that of said ball; and also, for the third joint, between the neck of said prosthesis, characterized in that it is smooth and without bumps or notches, and preferably slightly flared, in order to permit the physiological circumduction movement of the joint with low friction and without wear, and between the bevel situated at the opening of the mobile cup, characterized in that this opening narrows toward the center of said mobile articular cup and has an internal diameter substantially equal to or less than that of the ball, its flared part being designed to adapt perfectly to that of the flared neck of the prosthesis, in all the respective positions of the mobile components when the neck comes into contact with the mobile cup and drives it in its course during a clearance of large amplitude.

This therefore is a device which, by combining the functions of systems already described elsewhere, provides an answer to the problems of wear and rapid deterioration and thus makes it possible to successfully treat all types of articular pathologies without wear, without luxation, and thus for a longer time and with a wide range of movements, by means of its triple joint.

The most important characteristics of the system according to the invention are set out again in the claims.

III. DESCRIPTION OF THE DRAWINGS AND EMBODIMENTS

Explanation of the Figures:

Other advantages and aspects of the invention will become clear from reading the following description which is given by way of example and in which reference is made to the attached drawings, where.

DESCRIPTION

Figure 1:
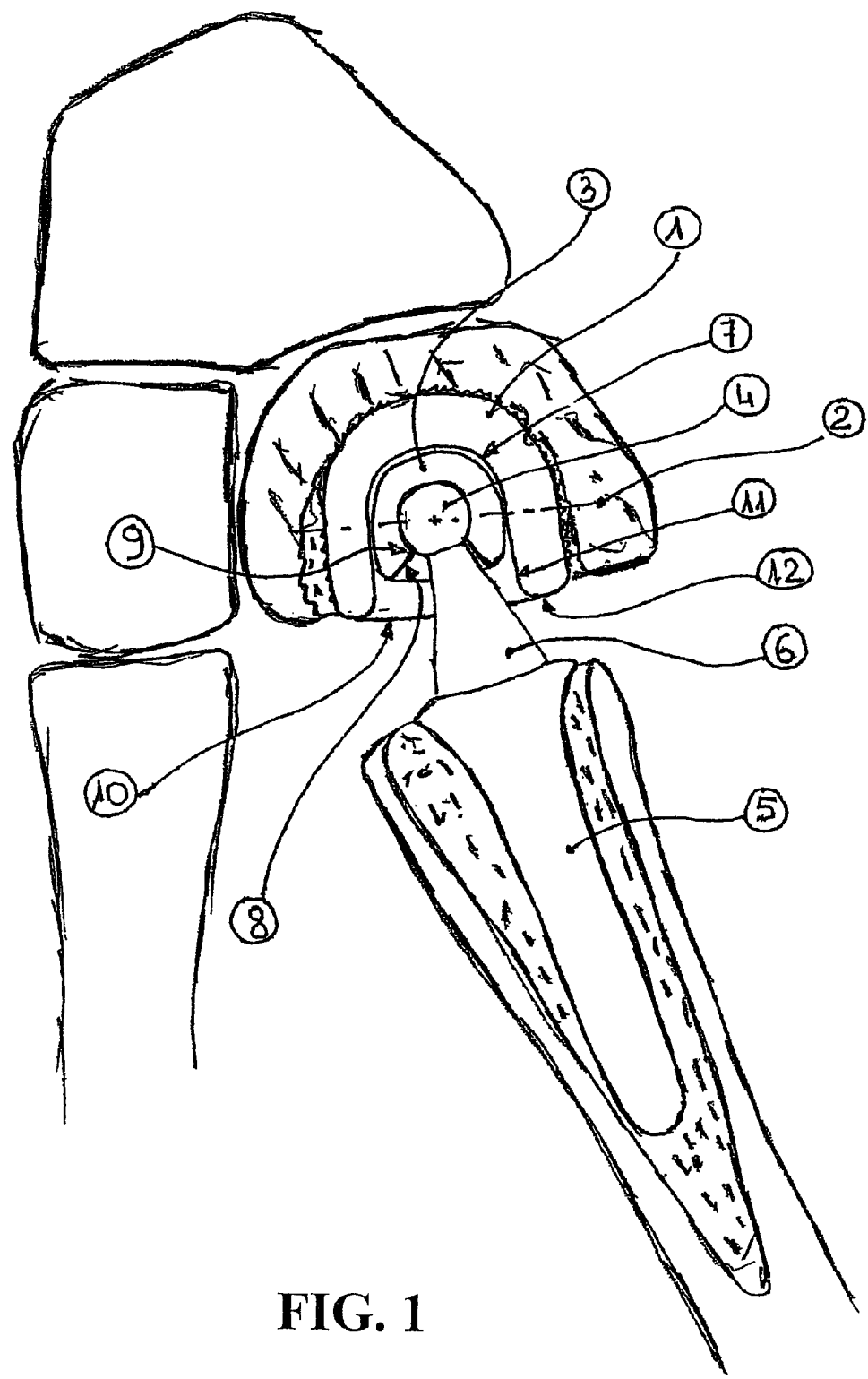
FIG. 1 is a perspective view of the bone joint system (1) comprising three articular components, namely a bone-anchoring shell (1) and an articular cup (3) in its mobile configuration sliding, on the one hand, on the head (4) of a femoral prosthesis (5) and, on the other hand, in the smooth cavity (7), formed as a sphere portion, of the bone-anchoring shell (1).
Figure 2:
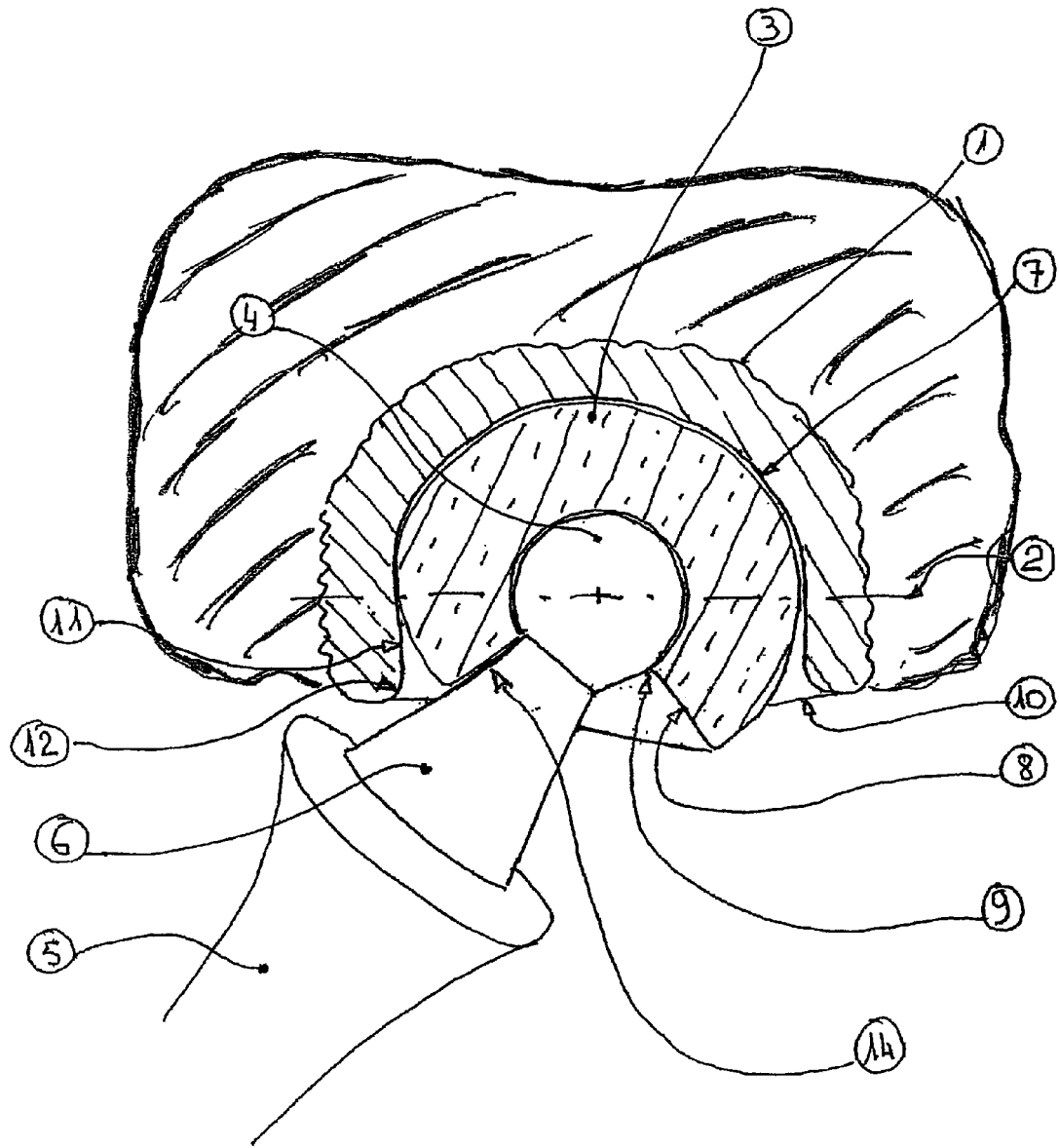
FIG. 2 is a detailed view showing the third joint with the characteristics claimed for the neck (6) and for the inner bevel (10) of the mobile cup (3). The invention is not limited to the embodiments shown in the attached drawings.
Figure 3:
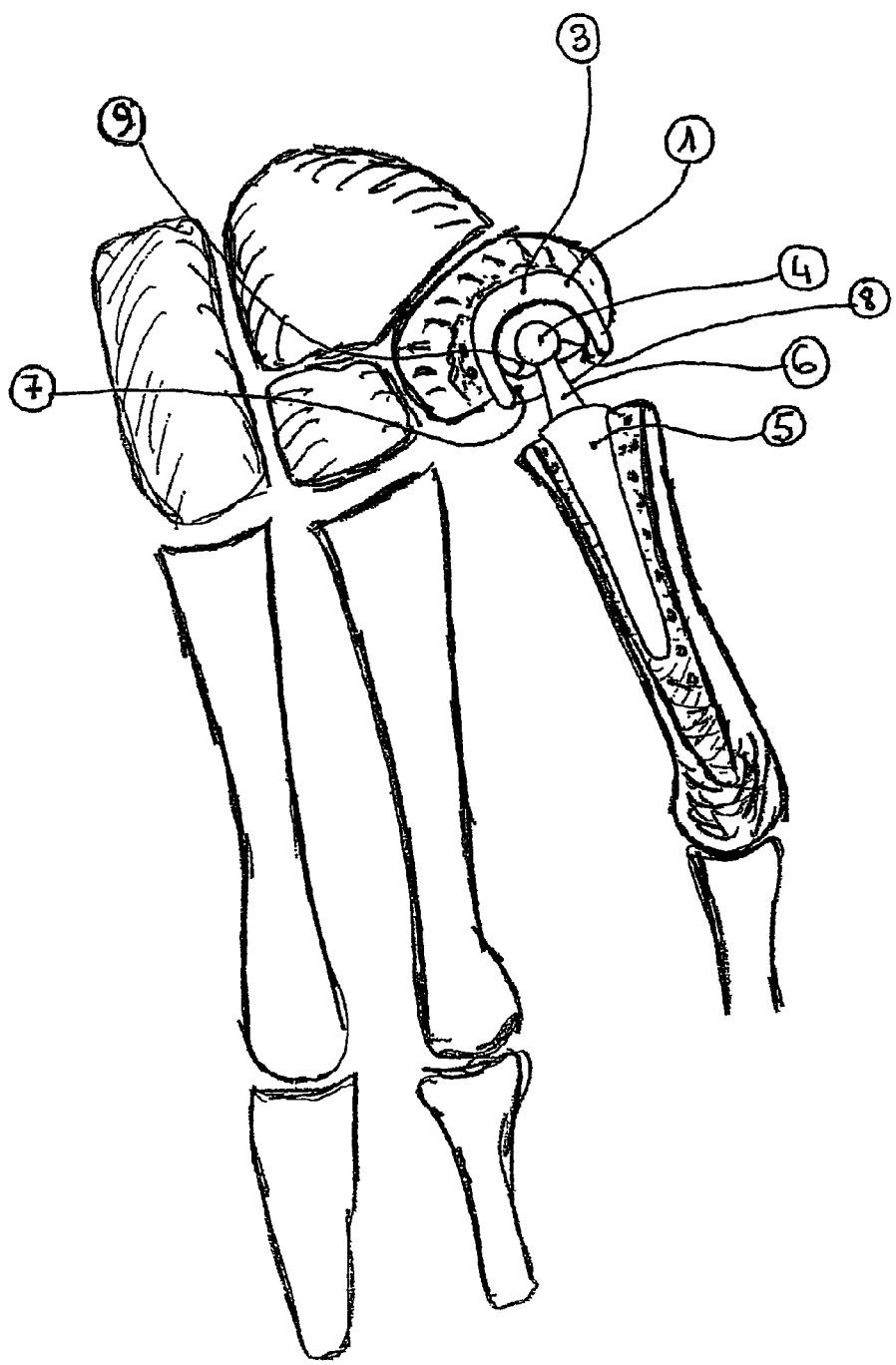
FIG. 3 is a detailed view of the bone joint system.

A system which is used to replace bone joints of substantially spherical geometry of the upper and lower limbs and which is made of biocompatible materials, characterized in that it comprises three articular components and a triple joint with three sliding contact surfaces for the displacements, namely:

A bone-anchoring shell (1) made of rigid biocompatible material and having, on its concave inner face, a smooth and substantially hemispherical articular surface (7) which is polished and has no bumps, cavities or reliefs that could cause wear of the mobile cup (3) or impede its free clearance when the latter is stressed in angular or rotary displacement by the neck (6) of the prosthesis (5), characterized in that its opening (10) is situated at a distance of between 1 and 6 mm beyond the equator (2) of said bone-anchoring shell (1) in such a way as to form a guide skirt (11), and it has a rounded edge (12) with a radius of between 1 and 5 mm, in order to avoid any abrasion of the mobile cup (3) during its introduction into said bone-anchoring shell (1) during surgery.

A prosthesis (5) comprising, at its part remote from the diaphyseal anchoring part, a polished ball (4) and a neck (6), characterized in that it is smooth without bumps or notches, and is preferably slightly flared, in order to permit the physiological circumduction movement of the joint with low friction and without wear.

A mobile articular cup (3) which slides, on the one hand, in the smooth cavity (7), shaped as a portion of a sphere, of the bone-anchoring shell (1) and, on the other hand, on the ball (4) and the neck (6) of a diaphyseal anchoring prosthesis (5), characterized in that its opening (8) narrows toward the center of said mobile articular cup (3) and has an internal diameter (9) substantially equal to or less than that of the ball (4), and its flared part is designed to adapt perfectly to the flared neck (6) of the prosthesis (5), in all the respective positions of the mobile components.

By virtue of its particular characteristics, said joint system permits, even in cases of revision or of poor bone quality, a successful, lasting and stable replacement that allows movements of wide amplitude without luxation or wear, for the ball-type joints of the upper or lower limbs.

More particularly:

The system which is used to replace bone joints of substantially spherical geometry and has a triple joint, of which the third joint is situated between the neck (6) of the prosthesis (5), smooth and without bumps or notches, and preferably slightly flared, and between the bevel situated at the opening of the mobile cup (3), is characterized in that its flare is between 1 and 15°, preferably 6°, in order to permit the physiological circumduction movement of the joint with low friction and without wear, and to adapt perfectly to that of the flared neck (6) of the prosthesis (5), in all the respective positions of the mobile components.

The system which is used to replace bone joints of substantially spherical geometry and has a triple joint, of which the third joint is situated between the neck (6) of the prosthesis (5), smooth and without bumps or notches, and slightly flared, preferably at 6°, in order to permit the physiological circumduction movement of the joint, and between the bevel situated at the opening of the mobile cup (3), is characterized in that the flare is defined by an angle corresponding to the angular clearance chosen, depending on the degree of freedom of the joint to be replaced, augmented by the angle of said neck (6) in order to form a contact (14) in perfect linear alignment of the two surfaces, so as to produce low friction, without wear, between the mobile components, in all their respective positions.

The system which is used to replace bone joints of substantially spherical geometry and has a triple joint, of which the second joint is situated between the polished articular surface of the ball (4) of a prosthesis (5) and between the inner face of the mobile cup (3), is characterized in that the surface area of said inner face is preferably greater than a hemisphere of diameter similar to that of the ball (4), and in that its opening (8) narrowing toward the center of said mobile articular cup (3) has an internal diameter (9) of less than 0.5 to 4 mm, preferably $1/10$th that of the ball (4), in order to reinforce the stability of said ball (4) in the mobile cup (3).

The invention claimed is:

1. A system which is used to replace bone joints of substantially spherical geometry and which is made of biocompatible materials, comprising:
   three articular components; and
   a triple joint with sliding contact surfaces for displacements,
   the three articular components including:
   a bone-anchoring shell that is made of a rigid biocompatible material and that has a concave inner face, on the inner face, the shell having a smooth and substantially hemispherical articular surface, which is polished and has no bumps, cavities or reliefs that could cause wear of a mobile cup or could impede its free clearance when the latter is stressed in rotary displacement by a neck of a prosthesis; and
   a prosthesis that includes, at a part remote from a diaphyseal anchoring part, a polished ball and a flared neck, which is smooth, without bumps or notches; and
   a mobile articular cup that slides, in the smooth inner face of the bone-anchoring shell, and on the ball and the neck of the prosthesis, said mobile cup having an opening that narrows toward a center of said mobile articular cup, and having a flared part that is designed to adapt perfectly to the neck of the prosthesis, in all the respective positions of the mobile components,
   the triple joint including a first joint that is situated between an outer face of the mobile articular cup and between the inner face of the bone-anchoring shell, and
   the inner face having an opening disposed at a distance of between 1 and 6 mm from an equator of the bone-anchoring shell toward the prosthesis, the opening being structured to form a guide skirt having a cylindrical part, the inner face having a rounded edge, the opening including the guide skirt having a radius of between 1 and 5 mm, the radius of the opening corresponding to a radius of the equator, the inner face being structured to avoid any abrasion of the mobile cup during its introduction into the bone-anchoring shell during surgery.

2. The system as claimed in claim 1, wherein:
   the triple joint has a third joint that is smooth and without bumps or notches and is slightly flared, the third joint being situated between the neck of the prosthesis, and between a bevel situated at the opening of the mobile cup, and
   the flare is between 1 and 15°, and is structured to permit the physiological circumduction movement of the joint with low friction and without wear, and to adapt perfectly to that of the flared neck of the prosthesis, in all the respective positions of the mobile components.

3. The system as claimed in claim 1, wherein:
   the triple joint has a third joint that is smooth and without bumps or notches and is slightly flared, the triple joint being situated between the neck of the prosthesis and between a bevel situated at the opening of the mobile cup, and being structured to permit the physiological circumduction movement of the joint, and
   the flare is defined by an angle corresponding to an angular clearance chosen, depending on a degree of freedom of the joint to be replaced, augmented by an angle of said neck, and is structured to form a contact in perfect linear alignment of the two surfaces, so as to produce low friction, without wear, between the mobile components, in all their respective positions.

4. The system as claimed in claim 1, wherein:
   the triple joint has a second joint that is situated between the polished articular surface of the ball and between the inner face of the mobile cup, and
   the opening of the inner face narrows toward the center of said mobile articular cup and has an internal diameter of less than 0.5 to 4 mm, the opening being structured to reinforce a stability of said ball in the mobile cup.

5. The system as claimed in claim 1, wherein the neck is slightly flared, and is structured to permit the physiological circumduction movement of the joint with low friction and without wear.

6. The system as claimed in claim 2, wherein the triple joint has a second joint that is situated between the polished articular surface of the ball and between the inner face of the mobile cup.

7. The system as claimed in claim 2, wherein the flare is 6°.

8. The system as claimed in claim 3, wherein the flare is 6°.

9. The system as claimed in claim 1, wherein the mobile articulator cup is made of a plastic biocompatible material.

10. The system as claimed in claim 4, wherein the internal diameter is $1/10^{th}$ that of the ball.

* * * * *